United States Patent [19]

Matza et al.

[11] Patent Number: 4,805,708

[45] Date of Patent: * Feb. 21, 1989

[54] CONTROLLING SULFIDE SCAVENGER CONTENT OF OIL-BASED DRILLING FLUID

[75] Inventors: Stephen D. Matza, Stafford; William E. Ellington; Henry C. Fleming, III, both of Houston, all of Tex.

[73] Assignee: Shell Oil Company, Houston, Tex.

[*] Notice: The portion of the term of this patent subsequent to Apr. 21, 2004 has been disclaimed.

[21] Appl. No.: 47,835

[22] Filed: May 6, 1987

[51] Int. Cl.[4] .................. G01N 31/02; G01N 33/24
[52] U.S. Cl. .................................. 175/40; 175/64; 436/25; 436/81; 436/120; 436/178
[58] Field of Search ............... 436/25, 81, 120, 178; 175/40, 64

[56] References Cited

U.S. PATENT DOCUMENTS

| | | | |
|---|---|---|---|
| 3,706,532 | 12/1972 | Noll | 23/230 R |
| 3,928,211 | 12/1975 | Browning et al. | 252/8.5 B |
| 4,252,655 | 2/1981 | Carney | 252/8.5 C |
| 4,658,914 | 4/1987 | Matza et al. | 436/81 X |

OTHER PUBLICATIONS

"H2S Detector Aids Drilling", by Steven H. Calmer, The analysts, Inc., Houston, Tex.; Oil & Gas Journal, Nov. 19, 1979.

"Chemical Scavengers for Sulfides in Water–Base Drilling Fluids", R. L. Garrett et al, Journal of Petroleum Technology, Jun. 1979.

Khristoforov, B. S., Krivospitskii, O. I., "Separate Determination of Metallic Zinc and Zinc Sulfide in Mixtures by Means of Iron (III) Chloride," *Chemical Abstracts*, vol. 72, 1970.

Sandell, E. B., "Colorimetric Determination of Traces of Metals," Interscience Publishers, Inc., NY, NY, Chapter XLVIIm pp. 449-450.

Hawley, G. G., *The Condensed Chemical Dictionary*, Tenth Edition, pp. 1106-1113, Van Nostrand and Reinhold Company publishers.

Carney, L. L., Jones, B., "Practical Solutions to Combat the Detrimental Effects of Hydrogen Sulfide During Drilling Operations," Society of Petroleum Engineers of AIME, Paper No. SPE 5198.

Garrett, R. L., "A New Field Method for the Quantitative Determination of Sulfides in Water–Base Drilling Fluids," *Journal of Petroleum Technology*, Sep. 1977, pp. 1195–1202.

Primary Examiner—Michael S. Marcus
Attorney, Agent, or Firm—Denise Y. Wolfs

[57] ABSTRACT

The concentration of unspent zinc-based hydrogen sulfide scavenger in an oil-based drilling fluid is controlled by selectively dissolving and extracting the unspent scavenger in a solvent, such as glacial acetic acid, separating the aqueous solution, measuring the concentration of dissolved zinc in the aqueous solution, for example, with an X-ray fluorescence spectrograph, and utilizing the results of the measurements to proportion the extent of changes in concentration of the scavenger in the drilling fluid.

20 Claims, No Drawings

CONTROLLING SULFIDE SCAVENGER CONTENT OF OIL-BASED DRILLING FLUID

BACKGROUND OF THE INVENTION

The present invention is applicable to substantially any process for drilling the borehole of a well with an oil-based drilling fluid in a location in which the wellbore may encounter hydrogen sulfide. Treatment of drilling fluid or mud is very important when drilling in areas where hydrogen sulfide ($H_2S$) may be encountered. $H_2S$ is a highly toxic and corrosive acidic gas having, at low concentrations, the distinctive odor of rotten eggs. When $H_2S$ enters the drilling fluid, it reacts with the alkaline drilling fluid and is converted into bisulfides ($HS^-$) and sulfides ($S^{-2}$).

The term "sulfides" as used here includes all water-soluble species, $H_2S$, $HS^-$, and $S^{-2}$, which co-exist in a sulfide-water system. The relative proportion of each species at equilibrium depends upon pH. For solutions with a pH of 7 to 13, typical for drilling fluids, bisulfides are the predominate species. If the pH drops below 7, $H_2S$ predominates, and above pH 13, sulfides predominate. Treatment of drilling mud with caustic soda and lime is often practiced where the presence of $H_2S$ is suspected. When soluble sulfide species accumulate in drilling mud, even small decreases in pH can generate large volumes of $H_2S$ gas in the drilling mud. To avoid reconversion of sulfides into $H_2S$, it is common practice to react the sulfides into a more chemically inert form, such as precipitation as an insoluble metal sulfide.

The term "sulfide scavenger" refers to any drilling fluid additive that can react with one or more sulfide species and can convert them to a more inert form. Scavenger compounds are added to the drilling fluid at levels sufficient to provide a slight excess of scavenging compound over the amount of $H_2S$ present or anticipated in the drilling fluid in order to ensure quick and complete removal. Zinc-based additives, such as zinc carbonate, zinc hydroxide and organic zinc compounds, provide effective scavenging by a rapid and irreversible reaction with sulfides to form solid zinc sulfide. The most prevalent commercial zinc-based scavengers are Mil-gard (Milchem), Coat 45 (Baroid) and Sulf-X(IMCO).

Zinc is often the preferred metal ion to react with sulfide because of its compatibility with drilling fluid and its effectiveness in precipitating sulfide ions. U.S. Pat. No. 3,928,211 describes a process for scavenging $H_2S$ from aqueous drilling fluids and describes several known processes for removing $H_2S$ from drilling fluids. A class at zinc carbonate, basic zinc carbonate, and zinc hydroxide are listed as effective for scavenging sulfide. U.S. Pat. 4,252,655 covers a process for removing sulfide ions from both water and oil-based drilling fluids with organic zinc chelates.

If the hydrogen sulfide can be chemically bound while in the borehole, then it will not reach the surface in a potentially hazardous form. If the reaction is fast enough, and pretreatment concentrations of scavenger are adequate, then pipe failure due to corrosion can also be avoided. Limiting the amount of scavenger added to that required for effective control of $H_2S$ entering the mud reduces operating costs and lessens the change of impairing mud rheology by overtreatment.

Previous field testing methods for determining sulfide scavenger requirements in drilling operations have focused upon sulfide analysis. U.S. Pat. No. 3,928,211 mentions that the amount of zinc required for scavenging may be determined by analyzing the mud for sulfide. U.S. Pat. No. 4,252,655 suggests the need to monitor drilling mud for sulfide ions to determine when additional zinc chelate must be added. A device called the "Mud Duck" described in "$H_2S$ Detector Aids Drilling Safety", by S. H. Calmer in Oil and Gas Journal, Nov. 19, 1979, page 160, continuously measures the total soluble sulfides in any aqueous mud system using ion-selective electrodes, and relates these measurements to the dissolved $H_2S$ gas in equilibrium with the mud.

A state of the art paper entitled "Chemical Scavengers for Sulfides in Water Based Drilling Fluids" by R. L. Garrett, R. K. Clark, L. L. Carney and C. K. Grantham, Sr. in the Journal of Petroleum Technology, June, 1979, page 787, discusses the chemistry of commercial scavengers, the parameters that affect the reliability of such materials and the problems affecting scavenger use. The Garrett Gas Train method for sulfide analysis is described as a simple, yet accurate field procedure for monitoring sulfides in drilling fluid filtrate. The same article describes a method developed by a service company that uses titration to analyze for total alkaline-soluble zinc, but not the reacted zinc product, zinc sulfide. The authors also identified a need for realistic rig-site monitoring test to measure the amount of available scavenger in drilling fluid.

Although there are many analytical techniques available for the quantitative determination of zinc, few are capable of differentiating forms of the metal. Speciation capability is critical for isolating unspent scavenger from spent scavenger (zinc which has reacted with sulfide to form zinc sulfide). These analytical methods which can offer speciation capability (X-ray diffraction, photoelectron spectroscopy) are inappropriate for field applications due to cost, lack of ruggedness, size, or extensive utility requirements. One solution to this dilemma is to invoke a chemical separation prior to an analysis for total zinc by a field-worthy method.

SUMMARY OF THE INVENTION

The present invention relates to determining the amount of unspent zinc-based sulfide scavenger which is present in an oil-based drilling fluid and to adjusting the scavenging capability of the drilling fluid as required during the drilling of a well. More particularly, the invention relates to a relatively quick and accurate procedure for measuring unspent zinc-based scavenger, which can be used in field locations. A determination is made of the amount of unspent zinc-containing sulfide scavenging material present in the drilling fluid. A measured volume of the drilling fluid is mixed with a significantly larger number of volumes (such as about 6 to 10 or more) of a selective solvent for dissolving zinc ions, and establishing with the resulting mixture a pH (such as a Ph of from about 4 to 6) at which substantially all the zinc in the drilling fluid, except for that combined into zinc sulfide molecules, becomes dissolved in the aqueous phase of the mixture. A portion of the resulting aqueous solution is separated from the solid components and any oil component of the drilling fluid, and the amount of zinc contained in the solids-free liquid is then determined, in order to identify the amount of unspent zinc-containing sulfide scavenger in the drilling fluid.

This process enables the drilling fluid to be sampled at a selected frequency and the concentrations of unspent scavenger to be promptly available to the mud engineers. For example, within about 30 minutes or so, based on such information, increases or decreases can be made in the rate of scavenger addition and for addition of scavenger-free fluid to the extent needed to quickly change the scavenger concentration to either avoid an impairment of the drilling fluid rheology or to quickly scavenge a sudden encounter of sulfides.

DESCRIPTION OF THE INVENTION

Applicants have discovered that changes in the concentration of zinc-based scavenger in a drilling mud can be accurately monitored at the well site, so that corrections in the rate of scavenger addition can be initiated in a timely fashion. Experiments have been conducted using samples of an oil-based drilling fluid typical of that used in drilling operations.

In a preferred embodiment of the invention, the drilling fluid sample is mixed with about 4 to 10 times its volume of glacial acetic acid, or a selective solvent which is substantially equivalent to glacial acetic acid with respect to selectively dissolving zinc ions which have not combined with sulfide ions. The concentration of zinc in the aqueous phase of the resulting solution is preferably measured with a portable X-ray fluorescence spectrographic unit which is, or is substantially equivalent to, a Portaspec Model 2501 portable X-ray spectrograph (available from Pitchford Scientific Instruments Division of the Hankison Corporation). The simplicity of the procedure and the equipment required make this method particularly applicable for use in field locations.

A preferred procedure for determining unspent zinc-based sulfide scavenger is described below.

SAMPLE PREPARATION

1. Transfer 10 ml of well mixed mud, minimizing any particle size exclusion, into a 150 ml beaker.
2. Add 60 ml of glacial acetic acid.
3. Heat at about 110° C. with frequent stirring for 10–15 minutes.
4. Allow the solution to cool until it is lukewarm to the touch (sufficient to prevent damage to a plastic centrifuge tube).
5. Place a portion of the mud-acetic acid mixture into a plastic centrifuge tube.
6. Centrifuge so that all the solids are firmly packed at the bottom of the centrifuge tube.
7. Accurately pipet 10 ml of the aqueous portion of the centrifuge solution into a Chemplex X-ray fluorescence counting vial.
8. Cover the counting vial with polypropylene film.

MEASUREMENTS BY X-RAY FLUORESCENCE

1. Position the element selector to zinc using the side-arm lever.
2. Turn on the X-ray fluorescence machine. Wait for the "ready" light and let warm 10 minutes.
3. Place the sample counting vial in the spring-loaded mount. Insert the mount into the sample chamber with the rounded edge of the stainless mount facing inward.
4. With X-rays on, adjust the current to read 0.5 milliamps.
5. Set the counting scaler on the front panel to 60 seconds.
6. Engage count pushbutton and record the final gross X-ray intensity counts on the digital readout.
7. Obtain gross X-ray counts for the glacial acetic acid blank and a calibration standard prepared by the dissolution of zinc oxide in glacial acetic acid.

CALCULATIONS:

Basis: 10 ml mud, 60 ml acetic acid, 10 ml aliquots in counting vial. Calculations are not valid for variations from these amounts.

1. Determine the net counts for samples and the zinc oxide calibration standard by subtracting the glacial acetic acid blank counts.
2. Determine the mg of zinc in 10 ml mud sample by the following ratio:

$$\text{mgs Zn in 10 ml mud} = \frac{\text{Net intensity}_{sample}}{\text{Net Intensity}_{Std}} \times \text{mg Zn}_{Std}$$

3. Determine pounds per barrel (lb/bbl) free zinc by multiplying the mg Zn in the 10 ml and sample by 0.035. The factor 0.035 is derived from the following conversion:

$$\frac{\text{lb Zn}}{\text{bbl mud}} = \frac{\text{mg Zn}}{\text{10 ml mud}} \times \frac{1000 \text{ ml}}{1 \text{ liter}} \times \frac{3.79 \text{ l}}{1 \text{ gal}} \times \frac{42 \text{ gal}}{1 \text{ bbl}} \times \frac{1 \text{ g}}{1000 \text{ mg}} \times \frac{1 \text{ lb}}{454 \text{ g}}$$

The selective solvent for zinc ions can include substantially any buffered liquid having a composition and concentration capable of providing a pH of about 4 to 6 when one part by volume of a drilling fluid having a pH in the range of from about 9 to 12 is mixed with about 4 to 10 parts by volume of the solvent. Exmaples of suitable selective solvents solutions include: glacial acetic acid, 10% formic acid, and 0.0001M hydrochloric acid. The concentration of zinc which becomes dissolved in the selective solvent can be measured by substantially any suitably accurate procedure. Procedures capable of being conducted in the field locations are preferred.

In situations in which the proportions found of unspent zinc-based scavenger are relatively low, an augmentive test for total zinc (including that combined into zinc sulfide molecules) can be performed by (a) an X-ray fluorescence measurement, or equivalent measurement, of the zinc in the unleached drilling mud, or (b) using as the solvent for dissolving zinc from the drilling fluid a strong acid, such as hydrochloric acid, as a solvent, for combined and noncombined zinc, prior to measuring the concentration of the zinc solution. Such an acid preferably has a normality of from about 1 to 3. The difference between the prior and augmentive tests will indicate whether the scavenger concentration was reduced by dilution of the drilling fluid, or by combination with sulfide.

The above described analyses and calculations are performed at the drilling site with a frequency which increases with a likelihood of the borehole encountering sulfides, and/or increases in the extent by which the zinc-based scavenger is found to have been depleted by round trips of the circulating drilling fluid. The amount of scavenger in the mud can then be adjusted to the extent required to provide effective control of sulfides without impairing the drilling fluid reology. The zinc-based sulfide scavengers are generally available as solids, and can be added as dry solids through a hopper for mixing solids with the circulating drilling mud, but the scavengers are preferably added in the form of slurries in aqueous liquids. In addition, as known in the art, a lignosulfonate treatment of the drilling fluid can be utilized for controlling any undersirable zinc-induced flocculation of mud components.

Various modifications of the invention described will become apparent to those skilled in the art from the foregoing description, and such modifications are intended to fall within the scope of the appended claims.

What is claimed is:

1. A process for determining the amount of unspent zinc-based sulfide scavenger in an oil-based drilling fluid, performed at a field location comprising:

mixing one part by volume of circulating oil-based drilling fluid from a well site with at least about 4 parts by volume of a selective solvent for zinc ions, which solvent establishes a mixture with a pH of no less than about 6 and is capable of dissolving substantially all of the zinc present in the drilling mud except for zinc ions that have been combined into molecules of zinc sulfides;

separating the resulting aqueous solution from any oil phase and undissolved solids; and measuring the amount of zinc in the aqueous solids-free solution in order to determine the amount of unspent zinc-based sulfide scavenger in the circulating oil-based drilling fluid.

2. The process of claim 1 in which the selective solvent for zinc is glacial acetic acid.

3. The process for claim 1 in which the amount of zinc in the aqueous solution is determined by measuring the amount of X-ray fluorescence exhibited by the solution.

4. The process of claim 1 in which the selective solvent for zinc is glacial acetic acid, the mixture of drilling fluid and selective solvent contains about 1 part by volume of the drilling fluid per 4 to 10 parts by volume of glacial acetic acid, and the amount of zinc dissolved in the aqueous solution is determined by a measurement of X-ray fluorescence.

5. The process of claim 4 in which the amount of zinc dissolved in the aqueous solution is determined by a portable X-ray fluorescence spectrographic unit.

6. The process of claim 1 in which an additional portion of the same drilling fluid is similarly mixed with a solvent consisting essentially of an aqueous strong acid solution capable of dissolving substantially all combined and non-combined zinc in the drilling fluid, with the amount of zinc in the aqueous solution being similarly measured to determine the decrease in scavenger due to drilling fluid dilution and reaction of scavenger with sulfides.

7. The process of claim 6 in which the strong acid is hydrochloric acid having a normality of about 1 to 3.

8. The process of claim 1 in which the amount of zinc dissolved in the selective solvent for zinc ions is determined by colorimetric analysis.

9. A process for drilling a well with an oil-based drilling fluid comprising:

(1) adding zinc-based scavengers to the oil-based drilling fluid for controlling encountered sulfide ions, (2) monitoring the drilling fluid to determine the amount of unspent zinc-based sulfide scavenger by:

(a) mixing one part by volume of a sample of circulating drilling fluid with at least 4 or more parts by volume of a selective solvent for zinc ions, with said solvent establishing a pH of less than about 6 and being capable of dissolving substantially all of the zinc present in the drilling fluid except for zinc ions combined into molecules of zinc sulfides;

(b) separating the resulting aqueous solution from any oil phase and undissolved solids; and (c) measuring the amount of zinc in the aqueous solution in order to determine the proportion of the unspent zinc-based sulfide scavenger in the circulating drilling fluids; and (3) adjusting the amount of scavenger in the circulating drilling fluid to the extent required to maintain an amount of scavenger in the drilling fluid sufficient to scavenge encountered sulfide ions.

10. The process of claim 9 in which the amount of zinc in the aqueous solution is determined by measuring the amount of X-ray fluorescence exhibited by the solution.

11. The process of claim 9 in which the selective solvent for zinc is glacial acetic acid.

12. The process of claim 9 in which the selective solvent for zinc is glacial acetic acid, the mixture of drilling fluid and selective solvent contains about 1 part by volume of the drilling fluid per 4 to 10 parts by volume of glacial acetic acid, and the amount of zinc dissolved in the aqueous solution is determined by a measurement of X-ray fluorescence.

13. The process of claim 9 in which an additional portion of the same drilling fluid is similarly mixed with solvent consisting essentially of an aqueous strong acid solution capable of dissolving substantially all combined and non-combined zinc in the drilling fluid, with the amount of zinc in the aqueous solution being similarly measured to determine the decrease in scavenger due to drilling fluid dilution and reaction of scavenger with sulfides.

14. The process of claim 13 in which the strong acid is hydrochloric acid having a normality of about 1 to 3.

15. The process of claim 9 in which the amount of zinc dissolved in the selective solvent for zinc ions is determined by colorimetric analysis.

16. The process of claim 9 in which the zinc-based sulfide scavenger is a zinc carbonate.

17. The process of claim 9 in which the zinc-based sulfide scavenger is basic zinc carbonate.

18. The process of claim 9 in which the zinc-based sulfide scavenger is an organic zinc chelate.

19. The process of claim 9 in which determinations of the proportion of unspent zinc-based scavenger in an oil-based drilling fluid are (a) initiated at a frequency which provides a rate of testing that varies with variations in the likelihood of the borehole encountering changed sulfide ion concentrations which change the extent to which the amount of unspent scavenger is different between the tests, (b) are conducted at the drill site and, (c) to the extent required, are utilized to proportion changes in the concentration of scavenger in the drilling fluid for keeping that concentration high enough to scavenge the sulfide being encountered.

20. A process for drilling a well with an oil-based drilling fluid comprising:

(1) adding zinc-based scavengers to the drilling fluid for controlling encountered sulfide ions, (2) monitoring the drilling fluid to determine the amount of unspent zinc-based sulfide scavenger by:

(a) mixing one part by volume of a sample of circulating drilling fluid with about 4 to 10 parts by volume of glacial acetic acid;

(b) separating the resulting aqueous solution from any oil phase and undissolved solids; and (c) determining the amount of zinc in the aqueous solution, by measuring the amount of X-ray fluorescence exhibited by the solution with a portable X-ray fluorescence spectographic unit, in order to determine the proportion of the unspent zinc-based sulfide scavenger in the circulating drilling fluid; and (3) adjusting the amount of scavenger in the circulating drilling fluid to the extent required to maintain an amount of scavenger in the drilling fluid sufficient to scavenge encountered sulfide ions.

* * * * *

UNITED STATES PATENT AND TRADEMARK OFFICE
CERTIFICATE OF CORRECTION

PATENT NO. : 4,805,708

DATED : February 21, 1989

INVENTOR(S) : Stephen Damian Matza, William Eugene Ellington, and Henry Creswell Fleming, III It is certified that error appears in the above—identified patent and that said Letters Patent is hereby corrected as shown below:

In column 5, line 17, delete "no".

Signed and Sealed this

Fifth Day of December, 1989

*Attest:*

JEFFREY M. SAMUELS

*Attesting Officer*     *Acting Commissioner of Patents and Trademarks*